(12) United States Patent
Ma et al.

(10) Patent No.: US 8,574,883 B2
(45) Date of Patent: Nov. 5, 2013

(54) METHOD OF CO-EXTRACTING MULTIPLE PROTEINS FROM CHICKEN EGG WHITE

(71) Applicant: Huazhong Agricultural University, Hubei (CN)

(72) Inventors: Meihu Ma, Hubei (CN); Fang Geng, Hubei (CN); Qun Huang, Hubei (CN)

(73) Assignee: Huazhong Agricultural University, Wuhan, Hubei Province (CN)

( * ) Notice: Subject to any disclaimer, the term of this patent is extended or adjusted under 35 U.S.C. 154(b) by 0 days.

(21) Appl. No.: 13/744,421

(22) Filed: Jan. 18, 2013

(65) Prior Publication Data

US 2013/0260437 A1  Oct. 3, 2013

(30) Foreign Application Priority Data

Mar. 27, 2012 (CN) .......................... 2012 1 0083362

(51) Int. Cl.
*C12N 9/36* (2006.01)
*C07K 1/00* (2006.01)
(52) U.S. Cl.
USPC .......................................... 435/206; 435/272
(58) Field of Classification Search
None
See application file for complete search history.

(56) References Cited

PUBLICATIONS

Omana, D. et al. "Co-extraction of egg white proteins using ion-exchange chromatography from ovomucin-removed egg whites" Journal of Chromatography B (2010) 878, 1771-1776.*
Dileep A. Omana et al. Co-extraction of egg white proteins using ion-exchange chromatography from ovomucin-removed egg whites. Journal of Chromatography B, Jul. 2010, vol. 878, issue 21, pp. 1771-1776.
M.C. Vachier et al. Isolation of hen egg white lysozyme, ovotransferrin and ovalbumin, using a quaternary ammonium bound to a highly crosslinked agarose matrix. Journal of Chromatography B, Feb. 1995, vol. 664, issue 1, pp. 201-210.

* cited by examiner

*Primary Examiner* — John S Brusca
*Assistant Examiner* — Gerard Lacourciere

(57) ABSTRACT

A method of co-extracting multiple proteins from chicken egg white is provided. Precipitate proteins step-by-step with polyethylene glycol, then separate the proteins via Q Sepharose Fast Flow anion-exchange chromatography. The method of co-extracting multiple proteins from chicken egg white is capable of obtaining five proteins simultaneously in one extraction process, and the protein products have high purity and high recovery ratio. And the method can be carried out only requiring common-used chromatographic filler, greatly reduces production cost, and provides favorable factors for large-scale industrial production of extracting protein from egg white.

11 Claims, 8 Drawing Sheets

METHOD OF CO-EXTRACTING MULTIPLE PROTEINS FROM CHICKEN EGG WHITE

BACKGROUND OF THE PRESENT INVENTION

1. Field of Invention

The present invention relates to a technical field of separation and purification for protein, and more particularly to a method of co-extracting multiple proteins from chicken egg white.

2. Description of Related Arts

With wide source, low price and protein content of over 80% in dry matter, chicken egg white is one of the best protein resources. Chicken egg white has excellent functional characteristics such as gelling, foaming and film forming, and is widely applied in fields of food processing industry and other manufacture industries and achieves tremendous application value. However, biological activity of the chicken egg white has more bright market prospects, e.g., important biological activities such as antimicrobial activity of lysozyme, iron-binding capacity of ovotransferrin, antiviral activity of ovomucin, and riboflavin-binding activity of ovoflavoprotein have already aroused strong concerns of researchers. Currently, as health of life has received more and more attention, egg white protein has huge potential application value in fields of health food and biomedicine for the biological activity thereof.

The conventional protein separation and purification techniques from chicken egg white are mainly for one kind or two kinds of proteins, and co-extracting techniques for multiple proteins are rarely reported in China. A few reports on co-extracting multiple proteins using liquid chromatography technique are disclosed in other countries. However, problems of low extraction efficiency, low protein purity, requiring various chromatographic fillers which are high in price and etc. are existed in the disclosed co-extracting method for multiple proteins. Thus, manufacture cost thereof is high and the application in large-scale industrial production is greatly limited.

SUMMARY OF THE PRESENT INVENTION

In order to fill technology blanks in China about co-extracting multiple proteins from egg white, an object of the present invention is to provide a method of co-extracting multiple proteins from chicken egg white, which has a good extraction effect, high purity, and is suitable for industrial production.

In order to accomplish the object mentioned above, a method of co-extracting multiple proteins from chicken egg white designed by the present invention comprises following steps of:

(1) diluting fresh egg white with 20~100 mmol/L NaCl solution of an equal volume, uniformly mixing, and adjusting PH to 5.0~8.0, so as to obtain processed egg white diluted solution;

(2) adding polyethylene glycol-8000 (PEG-8000) to the egg white diluted solution while stirring, until mass percentage concentration of the PEG-8000 is 2~6%, and preferably 2.7~4.5%, fully stirring for 2~12 hours, and then processing centrifugation to obtain precipitate A and supernatant A, continually adding PEG-8000 to the supernatant A until mass percentage concentration of the PEG-8000 is 8~12%, preferably 8.6~10.0%, fully stirring for 2~12 hours, then processing centrifugation to obtain precipitate B and supernatant B, continually adding PEG-8000 to the supernatant B until mass percentage concentration of the PEG-8000 is 14~18%, and preferably 14.8~16.3%, fully stirring for 2~12 hours, then processing centrifugation to obtain precipitate C and supernatant D, wherein the time of the fully stirring in the step (2) is preferred 2~4 hours;

(3) suspending the precipitate A in 200~800 mmol/L NaCl solution, fully stirring, centrifuging after suspending for 4~24 hours to obtain new precipitate, suspending the new precipitate in distilled water, fully stirring, centrifuging, suspending in distilled water again and processing centrifugation again, so as to wash away sodium chloride, collecting precipitate, so as to obtain ovomucin;

(4) separating the precipitate B, the precipitate C and the supernatant D by Q Sepharose Fast Flow anion-exchange chromatography, processing stepwise elution with sodium chloride solution, respectively collecting, dialyzing, and then freeze-drying each elution peak to obtain multiple protein products to be identified; and (5) identifying the multiple protein products to be identified by sodium dodecyl sulphate polyacrylamide gel electrophoresis (SDS-PAGE), merging protein products of a same kind, so as to obtain lysozyme, ovotransferrin and ovalbumin Preferably, the stepwise elution through sodium chloride solution in the step (4) is processed by respectively employing Tris-HCl buffer solution containing NaCl of 0.05~0.12 mmol/L, 0.15~0.25 mmol/L and 0.28~0.50 mmol/L one by one at the same flow velocity, and more preferably, Tris-HCl buffer solution containing NaCl of 0.07~0.09 mmol/L, 0.16~0.21 mmol/L and 0.29~0.40 mmol/L one by one at the same flow velocity.

Preferably, PH of the Tris-HCl buffer solution is 7.0~8.5 and a concentration thereof is 10~100 mmol/L. The flow velocity of the Tris-HCl buffer solution containing NaCl is 2.0~3.0 mL/min.

The method of co-extracting multiple proteins from chicken egg white of the present invention is capable of simultaneously obtaining five proteins at a time, i.e., the ovomucin, the lysozyme, the ovotransferrin, the ovalbumin and the ovoflavoprotein. Thus, compared with the conventional method of separation one or two proteins from egg white, the method of the present invention improves extraction efficiency and utilization rate of raw material.

Technology roadmap employed by the method of the present invention is polyethylene glycol fractional precipitation for pre-separation and ion-exchange column chromatography for purification. Compared with an ammonium sulfate precipitation method often employed in conventional art, the polyethylene glycol fractional precipitation has following advantages.

1. Mild conditions thereof is beneficial to maintain native conformation and biological activity of proteins.
2. Without a desalting treatment, the protein product obtained can be directly processed with Q Sepharose Fast Flow anion-exchange chromatography after being dissolved, which shortens cost of time thereof for approximately 24 hours and reduces a large amount of distilled water consumed thereof.
3. The polyethylene glycol is stable in property, not harmful to the environment, and causes no problems of water eutrophication.

In a process of the pre-separation, multiple kinds of proteins are separated effectively by optimizing concentration range of polyethylene glycol-8000, wherein all of the ovomucin is present in the precipitate A, the ovoflavoprotein are mainly present in the precipitate B, the lysozyme and the ovotransferrin are mainly present in the precipitate B and the precipitate C, and most of the ovalbumin are present in the supernatant D. Each protein has a good purity in corresponding precipitate, in such a manner that high purity protein is obtained by employing one kind chromatographic filler only in the follow-up process of Q Sepharose Fast Flow anion-exchange chromatography and requiring no exchange of the chromatographic filler, which simplifies operation step thereof, and shortens the time of protein extraction. The Q Sepharose Fast Flow anion-exchange chromatography in the present application only employs commonly used chromatographic filler, has low price and stable property, and is suitable for industrial application. Technical parameters corresponded thereof does not need to be further optimized in the process of expanding the production scale from a laboratory to industrial production.

Beneficial effects of the present invention are following. The method of co-extracting multiple proteins from chicken egg white is capable of obtaining five proteins simultaneously in one extraction process, and the protein products have high purity and high recovery ratio. And the method can be carried out by only requiring common-used chromatographic filler, greatly reduces production cost, and provides favorable factors for large-scale industrial production of extracting protein from egg white.

These and other objectives, features, and advantages of the present invention will become apparent from the following detailed description, the accompanying drawings, and the appended claims.

Figure 1:
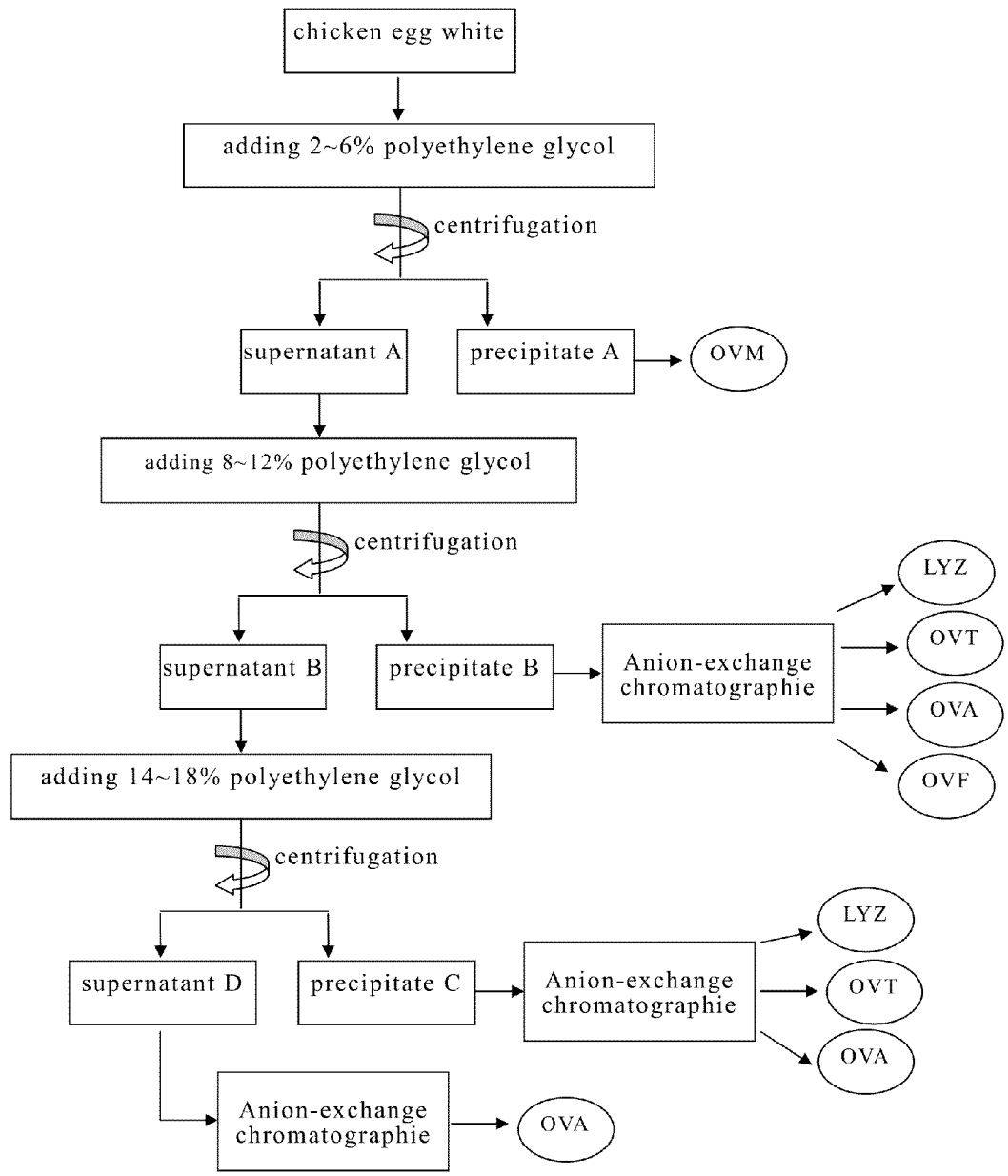
FIG. 1 is a flow chart of a method of co-extracting multiple proteins from chicken egg white according to a preferred embodiment of the present invention.

In the drawings, OVM refers to ovomucin, LYZ refers to the lysozyme, OVT refers to the ovotransferrin, OVA refers to the ovalbumin, OVF refers to the ovoflavoprotein, and EW refers to egg white.

DETAILED DESCRIPTION OF THE PREFERRED EMBODIMENT

Further description is illustrated in detail combining with the accompanying drawings and the preferred embodiment.

Embodiment 1

Figure 2:
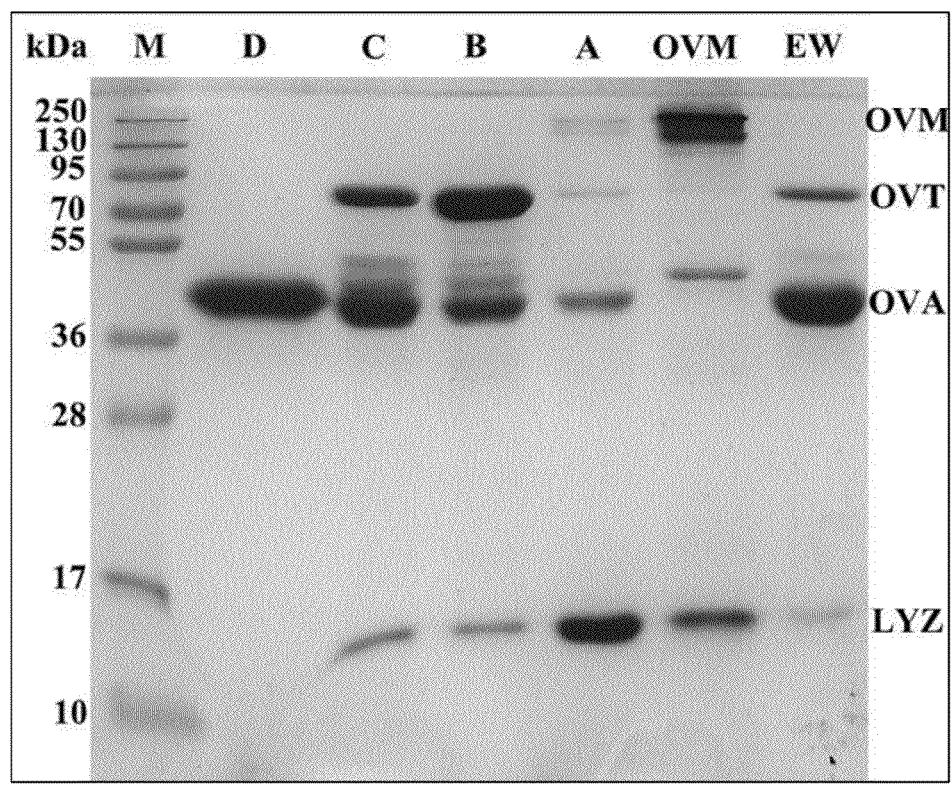
FIG. 2 is an SDS-PAGE pattern of precipitate A, precipitate B, precipitate C, supernatant D and OVM
Figure 3:
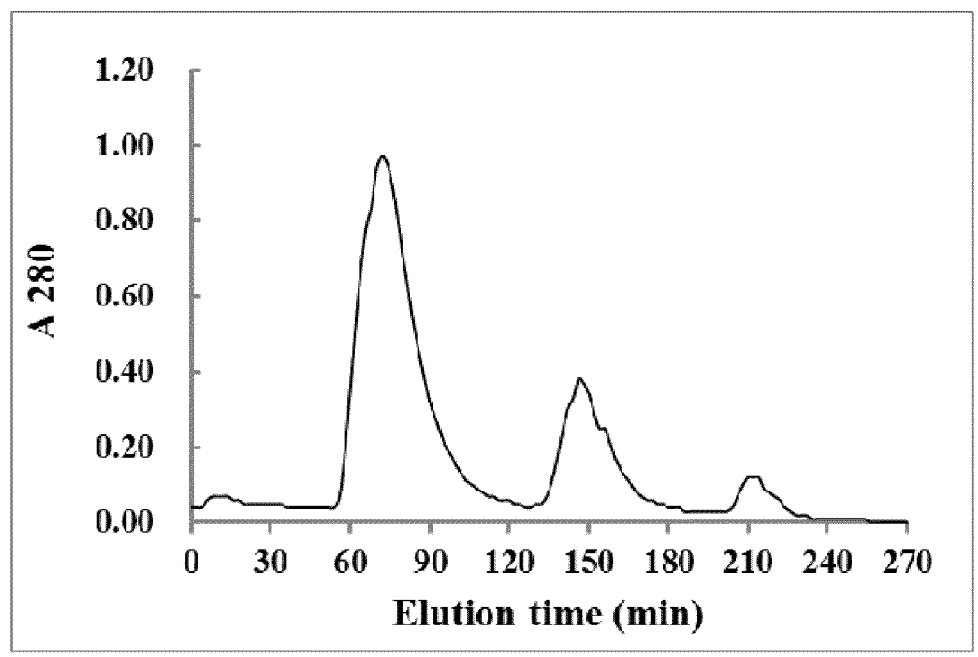
FIG. 3 is an anion-exchange chromatogram of the precipitate B.
Figure 4:
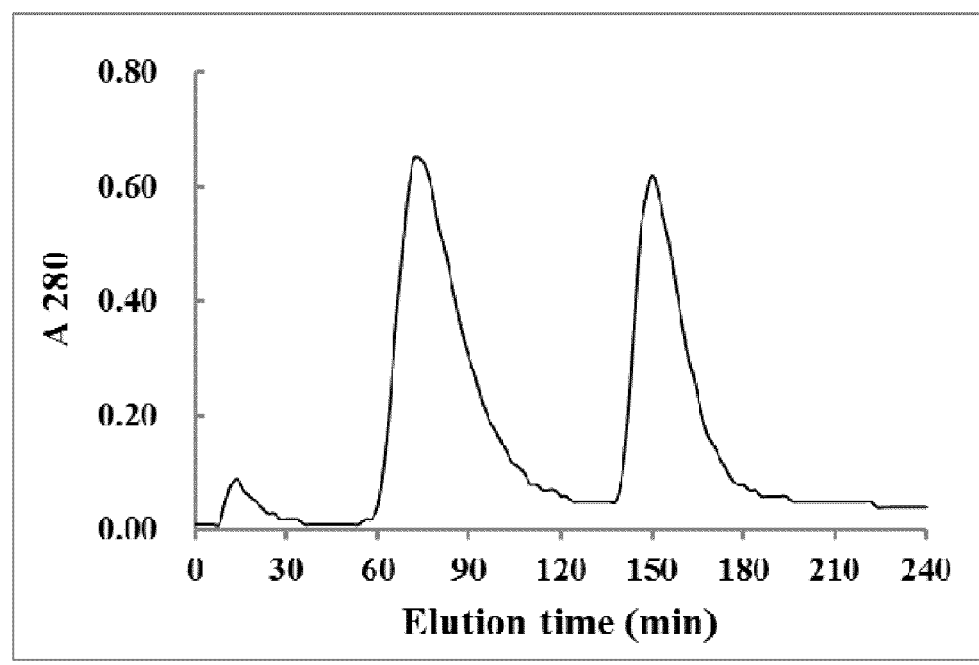
FIG. 4 is an anion-exchange chromatogram of the precipitate C.
Figure 5:
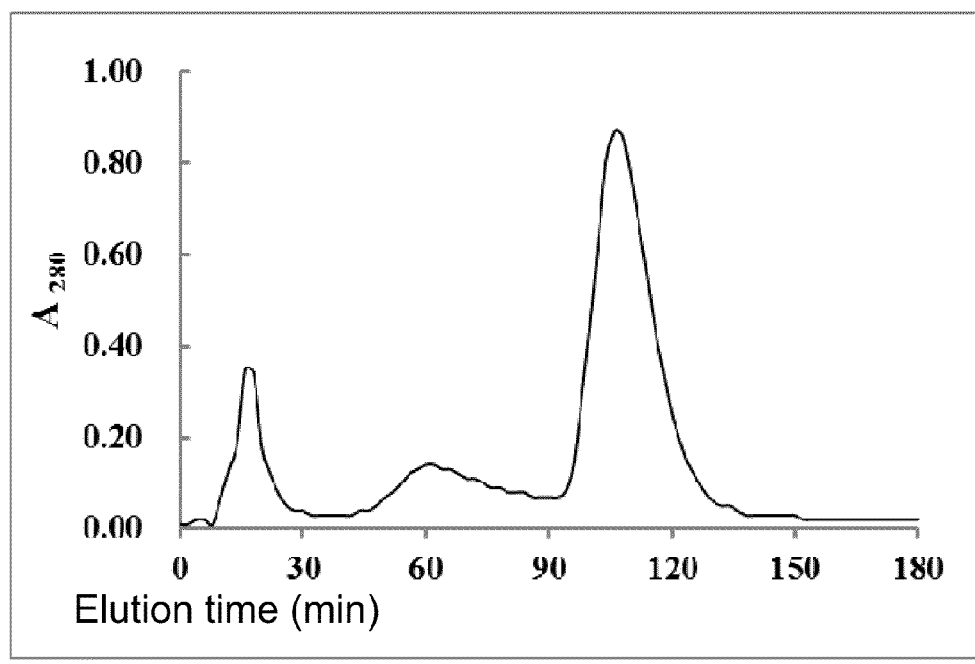
FIG. 5 is an anion-exchange chromatogram of the supernatant D.
Figure 6:
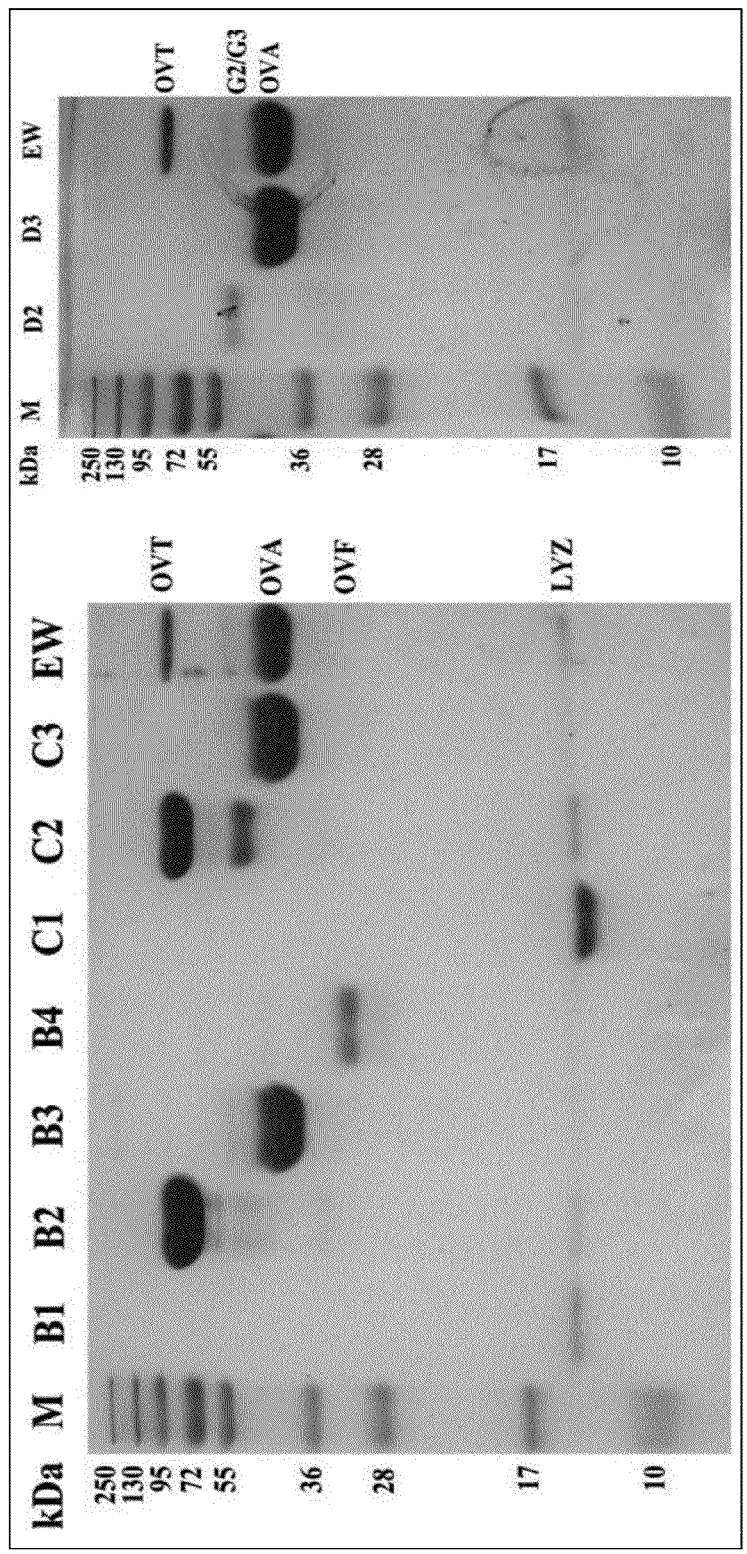
FIG. 6 is an SDS-PAGE pattern of peaks obtained by anion-exchange chromatography of the precipitate B, the precipitate C and the supernatant D.
Figure 7:
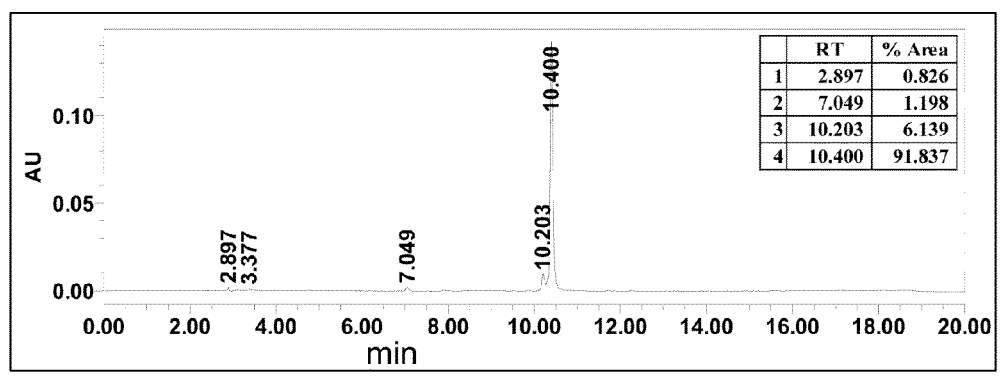
FIG. 7 is an HPLC (High Performance Liquid Chromatography) chromatogram of a lysozyme product.
Figure 8:
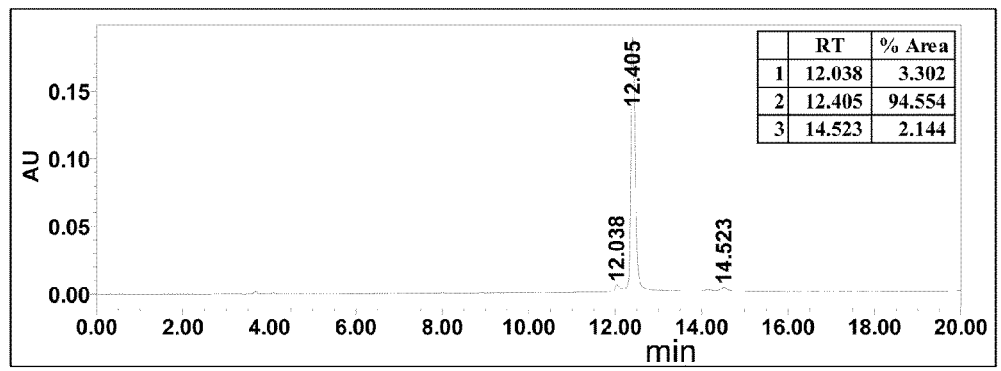
FIG. 8 is an HPLC chromatogram of an ovotransferrin product.
Figure 9:
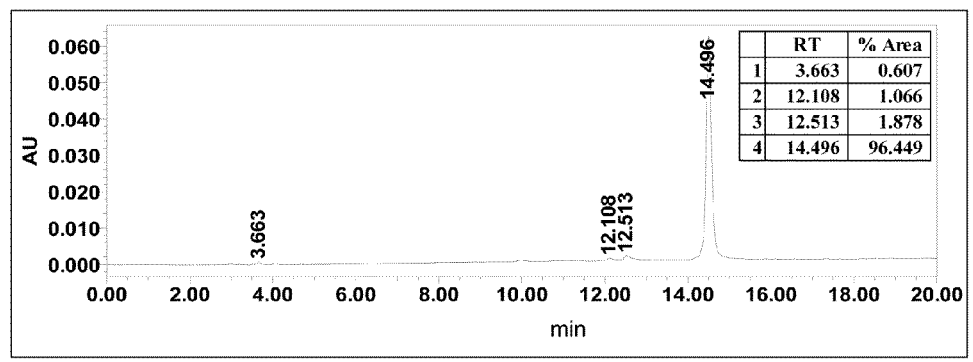
FIG. 9 is an HPLC chromatogram of an ovalbumin product.
Figure 10:
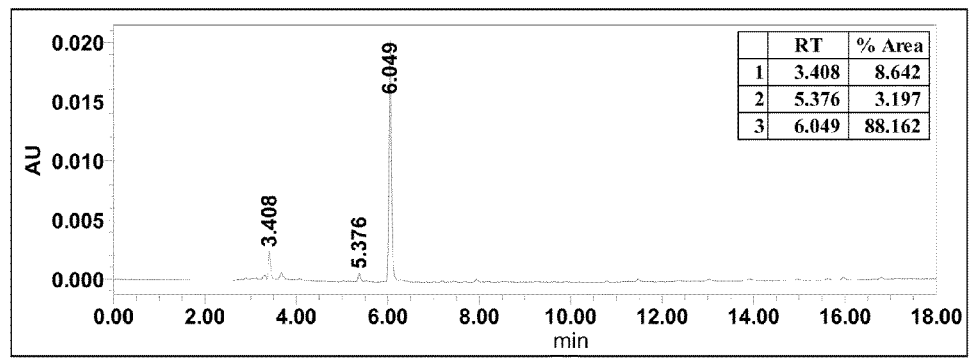
FIG. 10 is an HPLC chromatogram of an ovoflavoprotein product.

A method of co-extracting multiple proteins from chicken egg white comprises at least one steps of:

1. pretreating sample, comprising:
   beating fresh eggs, separating egg white and egg yolk, and collecting the egg white;
2. extracting protein, comprising:
   (1) adding 50 mmol/L NaCl solution of an equal volume to 1.0 L egg white while stirring, stirring for 2 hours to be well mixed, and adjusting PH to 6.0, in such a manner that egg white diluted solution which is well processed is obtained,
   (2) adding polyethylene glycol-8000 (PEG-8000) to the egg white diluted solution while stirring until mass percentage concentration of the PEG-8000 is 2.7~4.5%, wherein precipitate is generated in the solution at this moment, magnetic stirring for 2 hours for fully diffusing, so as to obtain suspension liquid, then processing centrifugation at 15000×g for 10 minutes under 4° C. to obtain precipitate A and supernatant A,
   (3) continually adding PEG-8000 to the supernatant A until mass percentage concentration of the PEG-8000 thereof is 8.6~10.0%, fully stirring for 2 hours, then processing centrifugation at 12000×g for 10 minutes to obtain precipitate B and supernatant B, and
   (4) continually adding PEG-8000 to the supernatant B until mass percentage concentration of the PEG-8000 thereof is 14.8~16.3%, fully stirring for 2 hours, then processing centrifugation at 12000×g for 10 minutes under 4° C. to obtain precipitate C and supernatant D, taking samples from the precipitate A, the precipitate B, the precipitate C and the supernatant D to process polyacrylamide gel electrophoresis (SDS-PAGE), wherein a result is shown in FIG. 2 from which proteins contained therein is capable of being identified preliminarily;
3. separating and purifying proteins thereof, comprising:
   (1) suspending the precipitate A in 500 mmol/L NaCl solution, stir for 4 hours at 4° C., then processing centrifugation at 15000×g for 10 minutes to remove most of lysozyme, ovalbumin and ovotransferrin, collecting precipitate A1 obtained, then suspending the precipitate A1 in distilled water for 2 hours, processing centrifugation again at 15000×g for 10 minutes, suspending in distilled water again to wash away NaCl, collecting precipitate, wherein 3.38 g ovomucin product is obtained after vacuum freeze-drying, SDS-PAGE of the ovomucin product obtained is shown as OVM of the FIG. 2, and purity of the ovomucin product obtained is 82.40% which is calculated via gel-pro analyzer version, and storing the ovomucin product at −20° C.,
   (2) separating the precipitate B, the precipitate C and the supernatant D via Q Sepharose Fast Flow anion-exchange chromatography, comprising following steps of:
   filling Q Sepharose Fast Flow anion-exchange chromatographic filler in a chromatography column having a size of 50×5 cm, flowing Tris-HCl buffer solution (pH=8.0, 20 mmol/L) at a speed of 2 mL/min for 2 hours in the chromatography column, so as to equalize the chromatography column,
   disposing the precipitate B into Tris-HCl buffer solution (pH=8.0, 20 mmol/L) to dissolve, centrifuging at 12000×g for 10 minutes under 4° C. to remove a small amount of insoluble substance, followed by filling into Q Sepharose Fast Flow anion-exchange chromatography column,
   washing the chromatography column with Tris-HCl buffer solution (pH=8.0, mmol/L) at a flowing speed of 2 mL/min, then respectively processing stepwise elution with Tris-HCl buffer solutions (pH=8.0, 20 mmol/L) at a same flowing speed and containing 0.07 mol/L, 0.16 mol/L and 0.40 mol/L NaCl, and
   collecting each peak generated in the stepwise elution respectively, dialyzing liquids collected at each peak four times with distilled water, followed by freeze-drying, wherein the precipitate C and the supernatant D are respectively separated by the same method, and as shown in FIGS. 3~5, freeze-dried powders B1, B2, B3, B4, C1, C2, C3, D1, D2 and D3 of multiple protein products to be identified which are respectively corresponding to every peaks of the precipitate B, the precipitate C and the supernatant D are obtained, (3) processing polyacrylamide gel electrophoresis (SDS-PAGE) identification by 12% polyacrylamide gel, comprising:

dissolving 10 mmg freeze-dried powders of the protein products to be identified in 5 ml double-distilled water, taking 80 mmL solution after fully dissolved, adding 20 mmL protein loading buffer solution which is 5 times concentration, heating about 5 minutes in boiling water bath after uniformly mixed, taking 5 mmL to fill into a sample adding hole, and processing electrophoresis at a constant voltage of 100V, after the electrophoresis is finished, fixing polyacrylamide gel for 30 minutes with fixing solution containing 50% ethanol and 10% acetic acid, staining for 30 minutes at 45° C. by Commassie Blue Staining Solution R-250 containing 0.1% R-250, 25% ethanol and 8% acetic acid, disposing into destaining solution containing 25% ethanol and 8% acetic acid to destain until background color thereof is destained and electrophoretic band is distinct, analyzing the electrophoretic band by software, and calculating relative molecular weight, wherein electrophoretogram obtained is shown as FIG. 6, a protein contained in B1 is the lysozyme, a protein contained in B2 is the ovotransferrin, protein contained in B3 is the ovalbumin, protein contained in B4 is the ovoflavoprotein, protein contained in C1 is the lysozyme, protein contained in C2 is the ovotransferrin, protein contained in C3 is the ovalbumin, D1 and D2 have no content of subject proteins, and protein contained in C3 is the ovalbumin, merging same kinds of protein, wherein 1.57 g lysozyme product is obtained after mixing B1 and C1, 15.51 g ovotransferrin product is obtained after mixing B2 and C2, 138.46 g ovalbumin product is obtained after mixing B3, C3 and D3, and B4 is 2.10 g ovoflavoprotein product; and 4. determining purity and calculating recovery, comprising following steps of:

(1) determining of protein content in protein products, wherein a content of protein in the ovomucin product is determined by kjeldah method, contents of protein in the lysozyme product, the ovotransferrin product, the ovalbumin product and the ovoflavoprotein product are determined by coomassie brilliant blue kit method, and determination results of protein content in each protein product are as following:

| Product | Ovomucin | Lysozyme | Ovotransferrin | Ovalbumin | Ovoflavoprotein |
|---|---|---|---|---|---|
| Protein content | 78.32% | 74.51% | 64.90% | 36.56% | 14.67% |

(2) determining purity of protein product, wherein purity of the ovomucin product has been determined in the step of separation and purification of the precipitate A by sodium dodecyl sulphate polyacrylamide gel electrophoresis (SDS-PAGE), purity of the lysozyme product, the ovotransferrin product, the ovalbumin product and the ovoflavoprotein product is determined by Grace Vydac C4 (214TP, 5 µm, 250×4.6 mm) reversed phase high-performance liquid chromatography (RP-HPLC), processing linear gradient elution using acetonitrile solution containing 0.1% trifluoroacetic acid (TFA) at a flow rate of 1.0 mL/min, comprising:

firstly, applying 5% acetonitrile solution to equalize a chromatography column for 5 minutes, improving concentration of the acetonitrile solution from 5% to 80% in 15 minutes, then reducing the concentration of the acetonitrile solution to 5% in one minute and maintaining for 4 minutes, maintaining temperature of the chromatography column maintains at 35° C., detect by a Waters e2695 photodiode detector at 280 nm, and processing integration to peak area by software, and then process quantitative calculation to purity of each protein products based on peak area ratio, wherein result of determination of each protein product is following (see FIGS. 6~10).

| Product | Ovomucin | Lysozyme | Ovotransferrin | Ovalbumin | Ovoflavoprotein |
|---|---|---|---|---|---|
| Purity | 82.40% | 91.84% | 94.55% | 96.45% | 88.16% |

(3) determining yield thereof wherein yield of each protein is calculated by weight, protein content and purity of each protein product obtained from purification process to 250 g egg white according to the formula given below:

$$\text{Yield (\%)} = \frac{\text{Dry weight of peak} \times \text{Protein content} \times \text{Protein purity}}{\text{Weight of } EW \times \text{Protein content of } EW \times \text{Theoretical content of the protein}} \times 100\%$$

It is worth mentioning that, according to literature report, protein content of fresh egg white is calculated by 10.2%, percentages of ovomucin, lysozyme, ovotransferrin, ovalbumin, ovoflavoprotein in a total protein of the egg white are respectively calculated by 3.4%, 3.5%, 12%, 54% and 0.5%, which are calculated as theoretical value to compare with protein products obtained in the preferred embodiment, and results are shown as following.

| Product | Ovomucin | Lysozyme | Ovotransferrin | Ovalbumin | Ovoflavoprotein |
|---|---|---|---|---|---|
| Product weight (g) | 3.38 | 1.57 | 15.51 | 138.46 | 2.10 |
| Protein content in the product | 78.32% | 74.51% | 64.90% | 36.56% | 14.67% |
| Purity of the product | 82.40% | 91.84% | 94.55% | 96.45% | 88.16% |
| Weight of protein in the product (g) | 2.18 | 1.07 | 9.52 | 48.82 | 0.27 |
| Theoretical weight protein in 250g egg white (g) | 3.47 | 3.57 | 12.24 | 55.08 | 0.51 |
| Recovery | 62.82% | 29.97% | 77.78% | 88.63% | 52.94% |

The table above indicates that the method of co-extracting multiple proteins from chicken white according to the preferred embodiment of the present invention obtains a satisfying recovery and a high purity.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of co-extracting multiple proteins from chicken egg white, comprising steps of:
    (1) diluting fresh egg white with 20~100 mmol/L NaCl solution of an equal volume, mixing, and adjusting pH to 5.0~8.0, so as to obtain processed egg white diluted solution;
    (2) adding polyethylene glycol-8000 (PEG-8000) to the egg white diluted solution while stirring, until the mass percentage concentration of the PEG-8000 is 2~6%, fully stirring for 2~12 hours, and then processing by centrifugation to obtain precipitate A and supernatant A, continually adding PEG-8000 to the supernatant A until the mass percentage concentration of the PEG-8000 is 8~12%, fully stirring for 2~12 hours, then processing by centrifugation to obtain precipitate B and supernatant B, and continually adding PEG-8000 to the supernatant B until the mass percentage concentration of the PEG-8000 is 14~18%, fully stirring for 2~12 hours, then processing by centrifugation to obtain precipitate C and supernatant D;
    (3) suspending the precipitate A in a 200800 mmol/L NaCl solution, stirring for 4~24 hours followed by centrifugation to obtain new precipitate, suspending the new precipitate in distilled water, fully stirring, centrifuging, suspending in distilled water again and processing centrifugation again, so as to wash away sodium chloride, collecting a precipitate, so as to obtain ovomucin;
    (4) separating the precipitate B, the precipitate C and the supernatant D individually by Q Sepharose Fast Flow anion-exchange chromatography, processing stepwise elution
    through sodium chloride solution, respectively collecting, dialyzing, and then freeze-drying each eluted peak to obtain multiple protein products to be identified; and
    (5) identifying the multiple protein products to be identified by sodium dodecyl sulphate polyacrylamide gel electrophoresis (SDS-PAGE), pooling protein products of a same kind, so as to obtain lysozyme, ovotransferrin and ovalbumin.

2. The method of co-extracting multiple proteins from chicken egg white, as recited in claim 1, wherein the stepwise elution through a sodium chloride solution in the step (4) is processed by respectively employing a Tris-HCl buffer solution containing NaCl of 0.05~0.12 mmol/L, 0.15~0.25 mmol/L and 0.28~0.50 mmol/L one by one which are at the same flow velocity.

3. The method of co-extracting multiple proteins from chicken egg white, as recited in claim 2, wherein pH of the Tris-HCl buffer solution is 7.0~8.5, the concentration of the Tris-HCl buffer solution is 10~100 mmol/L, and the flow velocity of the Tris-HCl buffer solution containing NaCl is 2.0~3.0 mL/min.

4. The method of co-extracting multiple proteins from chicken egg white, as recited in claim 1, wherein the step (2) comprises:
    adding polyethylene glycol-8000 (PEG-8000) to the egg white diluted solution while stirring 2~4 hours until the mass percentage concentration of the PEG-8000 is 2.7~4.5%, then processing by centrifugation to obtain the precipitate A and the supernatant A,
    continually adding PEG-8000 to the supernatant A while stirring for 2~4 hours until the mass percentage concentration of the PEG-8000 is 8.6~10.0%, then processing by centrifugation to obtain the precipitate B and the supernatant B, and
    continually adding PEG-8000 to the supernatant B until the mass percentage concentration of the PEG-8000 is 14.8~16.3%, fully stirring for 2~4 hours, then processing by centrifugation to obtain the precipitate C and the supernatant D.

5. The method of co-extracting multiple proteins from chicken egg white, as recited in claim 2, wherein the step (2) comprises:
    adding polyethylene glycol-8000 (PEG-8000) to the egg white diluted solution while stirring until the mass percentage concentration of the PEG-8000 is 2.7~4.5%, fully stirring for 2~4 hours, then processing by centrifugation to obtain the precipitate A and the supernatant A,
    continually adding PEG-8000 to the supernatant A until the mass percentage concentration of the PEG-8000 is 8.6~10.0%, fully stirring for 2~4 hours, then processing by centrifugation to obtain the precipitate B and the supernatant B, and
    continually adding PEG-8000 to the supernatant B until the mass percentage concentration of the PEG-8000 thereof is 14.8~16.3%, fully stirring for 2~4 hours, then processing by centrifugation to obtain the precipitate C and the supernatant D.

6. The method of co-extracting multiple proteins from chicken egg white, as recited in claim 3, wherein the step (2) comprises:
    adding polyethylene glycol-8000 (PEG-8000) to the egg white diluted solution while stirring until the mass percentage concentration of the PEG-8000 is 2.7~4.5%, fully stirring for 2~4 hours, then processing by centrifugation to obtain the precipitate A and the supernatant A,
    continually adding PEG-8000 to the supernatant A until the mass percentage concentration of the PEG-8000 is 8.6~10.0%, fully stirring for 2~4 hours, then processing centrifugation to obtain the precipitate B and the supernatant B, and
    continually adding PEG-8000 to the supernatant B until the mass percentage concentration of the PEG-8000 is 14.8~16.3%, fully stirring for 2~4 hours, then processing centrifugation to obtain the precipitate C and the supernatant D.

7. The method of co-extracting multiple proteins from chicken egg white, as recited in claim 2, wherein the stepwise elution through sodium chloride solution in the step (4) is processed by respectively employing Tris-HCl buffer solution containing NaCl of 0.07~0.09 mmol/L, 0.16~0.21 mmol/L and 0.29~0.40 mmol/L one by one which are at the same flow velocity.

8. The method of co-extracting multiple proteins from chicken egg white, as recited in claim 3, wherein the stepwise elution through sodium chloride solution in the step (4) is processed by respectively employing Tris-HCl buffer solution containing NaCl of 0.07~0.09 mmol/L, 0.16~0.21 mmol/L and 0.29~0.40 mmol/L one by one which are at the same flow velocity.

9. The method of co-extracting multiple proteins from chicken egg white, as recited in claim 4, wherein the stepwise elution through sodium chloride solution in the step (4) is processed by respectively employing Tris-HCl buffer solution containing NaCl of 0.07~0.09 mmol/L, 0.16~0.21 mmol/L and 0.29~0.40 mmol/L one by one which are at the same flow velocity.

10. The method of co-extracting multiple proteins from chicken egg white, as recited in claim 6, wherein the stepwise elution through sodium chloride solution in the step (4) is processed by respectively employing Tris-HCl buffer solution containing NaCl of 0.07~0.09 mmol/L, 0.16~0.21 mmol/L and 0.29~0.40 mmol/L one by one which are at the same flow velocity.

11. Multiple proteins co-extracted according to the method of claim 1.

* * * * *